United States Patent [19]

Grate et al.

[11] Patent Number: 4,705,883

[45] Date of Patent: * Nov. 10, 1987

[54] CARBONYLATION PROCESS

[75] Inventors: John H. Grate; David R. Hamm, both of Mountain View, Calif.; Donald H. Valentine, Ridgefield, Conn.

[73] Assignees: Catalytica Associates, Mountain View, Calif.; Haldor Topsoe, Copenhagen, Denmark

[ * ] Notice: The portion of the term of this patent subsequent to Jul. 15, 2003 has been disclaimed.

[21] Appl. No.: 820,850

[22] Filed: Jan. 24, 1986

Related U.S. Application Data

[63] Continuation-in-part of Ser. No. 532,784, Sep. 16, 1983, Pat. No. 4,600,793, and a continuation-in-part of Ser. No. 532,785, Sep. 16, 1983, Pat. No. 4,603,216, and a continuation-in-part of Ser. No. 707,885, Mar. 4, 1985, Pat. No. 4,629,804, and a continuation-in-part of Ser. No. 744,951, Jun. 17, 1985, and a continuation-in-part of Ser. No. 806,389, Dec. 9, 1985.

[51] Int. Cl.[4] ................ C07C 125/065; C07C 125/073
[52] U.S. Cl. ........................................ 560/25; 560/24
[58] Field of Search ..................................... 560/24, 25

[56] References Cited

U.S. PATENT DOCUMENTS 4,411,820 10/1983 Pretzer et al. .................... 560/24 X
4,474,978 10/1984 Drent et al. ............................ 560/24
4,491,670 1/1985 Bhaduri et al. ....................... 560/24

*Primary Examiner*—Werren B. Lone
*Attorney, Agent, or Firm*—Robert J. Baran; John H. Grate

[57] ABSTRACT

The invention providess a process for carbonylating a nitrogen-containing organic compound, selected from the group consisting of nitro, nitroso, azo, and azoxy compounds, by reacting said nitrogen-containing organic compound, with carbon monoxide, wherein the improvement comprises the step of:

(a) reacting said nitrogen-containing compound with carbon monoxide, in the presence of a primary amine and a catalyst, essentially free of redox active metal components selected from the group consisting of rhodium and ruthenium.

19 Claims, No Drawings

CARBONYLATION PROCESS

CROSS REFERENCE TO RELATED PATENT APPLICATIONS

This patent application is a continuation-in-part of U.S. patent applications Ser. Nos. 532,784 now U.S. Pat. No. 4,600,793 and 532,785, now U.S. Pat. No. 4,603,216 filed on Sept. 16, 1983; U.S. Ser. No. 707,885, now U.S. Pat. No. 4,629,804 filed on Mar. 4, 1985; U.S. Ser. No. 744,951, filed on June 17, 1985 and U.S. Ser. No. 806,389, filed on Dec. 9, 1985; all of which patents are entitled PROCESS FOR THE PREPARATION OF URETHANES and are hereby incorporated by reference.

BACKGROUND OF THE INVENTION

1. Field of the Invention

This invention relates to a process for the carbonylation of a nitrogen-containing organic compound by reacting said compound with carbon monoxide in the presence of a rhodium or ruthenium catalyst.

2. Description of the Art

Various patents have disclosed methods for carbonylating nitrogen-containing organic compounds—e.g., nitro compounds, amines, azo- and azoxy compounds,—to urethanes in the presence of a platinum group metal-containing catalyst usually a palladium or rhodium-containing catalyst and most often a palladium or rhodium halide-containing catalyst. Generally, a co-catalyst (promoter) has been needed in combination with the platinum group metal-containing catalyst in order to obtain improved rates of reaction. The vast majority of prior art processes use, as a co-catalyst, a halide salt of a metal which is redox-active under the reaction conditions, usually iron, and most often iron chlorides. The co-catalyst is used in substantial molar excess compared to the main catalyst in order to obtain the desired reaction rate. These large quantities of redox-active metal halides are troublesome to separate from the reaction product and cause substantial corrosion problems.

A few references have taught the addition of a primary amino compound (and/or related compounds, such as urea, biurets, and allophanates) to further improve the rate and selectivity of reactions catalyzed by a platinum group metal compound in combination with a redox-active metal halide-cocatalyst. U.S. Pat. No. 4,178,455 discloses that, in a process for converting nitroaromatic to urethane catalyzed by a platinum, palladium, rhodium, or ruthenium compound and a Lewis-acid promoter, the rate and selectivity are improved by adding to the reaction, an organic primary amino compound, a urea compound, a biuret compound, an allophanate compound, or a mixture thereof. The preferred Lewis acid promoters are redox-active metal salts, especially iron chlorides. This patent illustrates (by example) only palladium catalysts with iron chloride promoters. A careful study of the examples reveals that the starting nitroaromatic and the primary amino compound (or related compound) are both converted, in net, to urethane. Thus, when the primary amino compound or urea compound contains the same aryl group as the starting nitroaromatic compound the reported yield of urethane, based on only the nitroaromatic converted, exceeds 100%. This patent also teaches the use of tertiary amines, e.g. pyridine, in large molar excess compared to the palladium catalyst to prevent corrosion. See also U.S. Pat. No. 4,169,269 wherein a tertiary amine, e.g. pyridine. in large molar excess is utilized to suppress corrosion in a process utilizing a catalyst system comprising (1) palladium, ruthenium, rhodium or compounds thereof, and (2) a Lewis Acid, e.g. ferric chloride. Similarly, U.S. Pat. Nos. 4,219,661; 4,262,130; and 4,339,592 teach palladium catalysts with iron oxide and iron chloride co-catalysts in which addition of tertiary amines is one embodiment.

U.S. Pat. No. 4,297,501 discloses a process in which mixtures of a primary amine and a nitroaromatic are carbonylated to urethane with a Group VIII noble metal compound and an oxychloride compound capable of undergoing redox reactions. In the preferred embodiment of U.S. Pat. No. 4,297,501, the nitroaromatic corresponds to the primary amine, and the patent teaches the following reaction stoichiometry:

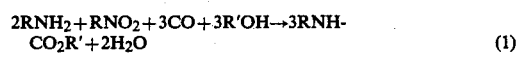
$$2RNH_2 + RNO_2 + 3CO + 3R'OH \rightarrow 3RNHCO_2R' + 2H_2O \quad (1)$$

U.S. Pat. No. 4,297,501 further teaches that when nitroaromatic is present in excess of the 1:2 ratio relative to amine, the remaining nitroaromatic is converted to urethane by the following reaction stoichiometry:

$$RNO_2 + 3CO + R'OH \rightarrow RNHCO_2R' + 2CO_2 \quad (2)$$

It can be seen from the above equations that when primary amine is initially present, in processes which convert nitroaromatic to urethane using Group VIII noble metals, the primary amine is, in net, consumed to also make urethane. (See equation (1) above). Once the primary amine is consumed to low levels, any remaining nitrobenzene is converted to urethane via reaction equation (2) above. Since the primary amine is already consumed to low levels, it is no longer available to favorably influence the rate of the process according to said reaction (2).

U.S. Pat. No. 4,304,922 similarly discloses a process in which mixtures of N,N'-diaryl urea and nitroaromatic are carbonylated to urethane with the same catalyst/co-catalyst systems of U.S. Pat. No. 4,297,501. Illustrated by examples are $PdCl_2$, $RhCl_3$, $IrCl_3$, $PtCl_4$ and $RuCl_3$ as Group VIII noble metal compounds. Iron oxychloride and several other redox active metal oxides and chlorides are illustrated as co-catalysts. In examples in which redox active metal oxides are used, anilinium hydrochloride is also added to provide active anionic chloride. In the preferred embodiment of this patent, the N,N'-diaryl urea and nitroaromatic have the same aryl groups, and the patent teaches that the following reaction stoichiometry is obtained:

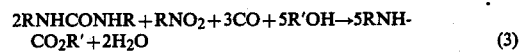
$$2RNHCONHR + RNO_2 + 3CO + 5R'OH \rightarrow 5RNHCO_2R' + 2H_2O \quad (3)$$

It is known that N,N'-diarylureas react with alcohols to produce urethane plus amine; see for Example U.S. Pat. No. 2,409,712, wherein the following reaction is disclosed:

$$RNHCONHR + R'OH \rightarrow RNHCO_2R' + RNH_2 \quad (4)$$

It can be seen that once this occurs under the reaction conditions, the same process as U.S. Pat. No. 4,297,501 is obtained according to equation (1) above. (Twice equation (4) plus equation (1) equals equation (3)). It can further be seen that both N,N'-diaryl urea and arylamine are, in net, consumed in the process to make urethane. Example 11 of U.S. Pat. No. 4,304,922 illustrates that when $RhCl_3$ is used as catalyst in combination with iron oxychloride as co-catalyst, nitrobenzene and N,N'-diphenylurea (1:2 molar ratio) are both consumed (100% and 99% conversion, respectively) to give urethane product 99% selectivity based on nitrobenzene plus N,N'-diphenylurea).

Japan Kokai No. 55-7227 discloses a process in which molecular hydrogen is added, to a process for carbonylating nitroaromatic, in the presence of a palladium catalyst, to increase the reaction rate. The description of the invention specifies a palladium catalyst, accompanied by promoters such as tertiary amines, iron and vanadium compounds, and chlorine ions. All illustrated examples use a supported palladiumselenium on carbon catalyst promoted with pyridine and either $FeCl_2$ or $VOCl_3$ (these are redox-active metal chlorides). The patent teaches that the addition of hydrogen causes hydrogenation of a fraction of the nitroaromatic to generate the corresponding primary arylamine in situ. The process is thus generically similar to that of U.S. Pat. No. 4,178,455, discussed above, which illustrates by example the addition of primary arylamine to a reaction with a supported palladium catalyst promoted with $FeCl_3$. Thus, it may be concluded that primary amine generated from hydrogen will in net be consumed in the reaction to make urethane. Indeed, Japan Kokai No. 55-7227 teaches that any primary amine remaining at the end of a reaction can be returned to another reaction with more nitroaromatic, in which case the primary amine is easily converted to urethane.

In U.S. Pat. No. 4,474,978 a process is disclosed for converting a nitroaromatic to a urethane in the presence of a primary amine and a catalyst system based on palladium complexed with Group VA-chelate ligands, including bis phosphine ligands and bis-tertiary amino-containing ligands. The patent teaches that redox active metal co-catalysts are not needed when these ligands are used. The patent teaches that the primary amine and/or urea are co-converted with the nitroaromatic to urethane. Thus, the process, in net, consumes added amine or urea. But, this patent does not suggest the use of ruthenium or rhodium with said ligands.

Thus, it is clear that, in the processes cited above, as the primary amine and/or urea compound is converted, in net, to urethane, its concentration decreases and its effects on reaction rate and selectivity must also decrease. Eventually, as nitroaromatic continues to be converted, either in a batch process or in a continuous process (with recycle of the remaining amine), the primary amine will be consumed to a low concentration. In order to maintain the improved rates and selectivities, which are obtained by the original addition of primary amine, urea, hydrogen, etc., it is necessary to provide additional primary amine, urea, hydrogen, etc. as the primary amine is consumed.

A few references teach the use of rhodium catalysts, in the absence of a redox-active metal co-catalysts, for the carbonylation of nitrogen-containing organic compounds to urethanes. However, these references do not teach the initial addition of primary amines, ureas, hydrogen, etc. to obtain improved activity. For example, U.S. Pat. No. 3,338,956 discloses a metal carbonyl catalyst of Group VIA, VIIA, or VIIIA for this reaction. The only such catalyst exemplified, however, is rhodium chlorocarbonyl and the rates of reaction are relatively slow.

U.S. Pat. No. 3,993,685 teaches the addition of tertiary amines, especially pyridine, to platinum group metal catalysts to obtain improved activity in the absence of redox-active metal co-catalysts. Rhodium chloride and hydridocarbonyl tris (triphenyl-phosphine) rhodium in combination with pyridine are exemplified.

U.S. Pat. No. 4,052,437 discloses the use of rhodium oxide as catalyst, preferentially in nitrilic solvent. $Rh_6(CO)_{16}$ as a catalyst is also exemplified in this patent. There is no suggestion that the initial addition of a primary aryl amine to the process disclosed in this patent would improve the rate.

An article in the Journal of Organic Chemistry 37, 2791 (1972) describes a reaction in which nitro-benzene in the presence of ethanol is carbonylated in low yield to urethane (<10%) and urea (<5%) with a catalyst comprising $Rh_6(CO)_{16}$ in pyridine solvent. The major product was aniline. A related article in Helvetica Chimica Acta 55, 2637 (1972) describes a reaction in which nitrobenzene is reacted with carbon monoxide and hydrogen to urea with a catalyst comprising $Rh_6(CO)_{16}$ in pyridine solvent. The pyridine is used in high concentration or excess to enable its function as a solvent for the reaction.

None of the above cited art, which discloses the use of rhodium catalysts (in the absence of redox-active metal co-catalysts) for the carbonylation of nitro-organics to urethanes, discloses the initial addition of primary amine, urea, hydrogen, etc. Moreover, the effect of initially adding primary amine to such catalysts is not predictable. Finally, the result obtained by adding a primary amine to a rhodium or ruthenium catalyst system essentially free from redox-active metal components, is substantially different from the result obtained when a primary amine is added to either Group VIII metal catalysts (including ruthenium, rhodium and palladium) in the presence of redox active metal co-catalysts or certain palladium catalysts in the absence of redox active metal co-catalysts.

Ruthenium compounds have been utilized in the reduction of organic nitro compounds to the corrresponding amines with mixtures of hydrogen and carbon monoxide. It was reported in U.S. Pat. No. 3,729,512 that urea is a byproduct of the reaction of nitrobenzene with hydrogen and carbon monoxide to give aniline using $Ru_3(CO)_{12}$ catalyst. It was also reported that the reduction of the organic nitro compound with carbon monoxide and ethanol, in the absence of $H_2$, resulted in a mixture of amine and a urethane. The patentee was not concerned with the preparation of a urethane product; therefore, there was no attempt to increase the selectivity above the approximately 22 percent, urethane, that was obtained.

It is an object of this invention to provide a process for the conversion of nitro-aromatic to urethane in good rate and selectivity, without requiring continual addition of primary amine, urea, hydrogen, etc. to maintain the rate and selectivity.

It is a further object of this invention to effectively carry out the above process in the absence of redox-active metal halide co-catalysts.

Other objects and advantages of this invention will become apparent from a careful reading of the specification below.

SUMMARY OF THE INVENTION

It has now been surprisingly found that, in a process for carbonylating nitrogen-containing organic compounds selected from the group consisting of nitro, nitroso, azo and azoxy compounds, by reacting said nitrogen-containing organic compound, with carbon monoxide, the improvement comprises:

(a) reacting said nitrogen-containing compound with carbon monoxide, in the presence of a primary amine and a catalyst, said catalyst being essentially free of redox active metal halide components, and comprising ruthenium or rhodium.

Furthermore, the present invention provides a process for converting a nitrogen-containing organic compound, selected from the group consisting of nitro, nitroso, azo, and azoxy compounds, into a carbamic acid derivative by reacting said nitrogen-containing organic compound with carbon monoxide wherein the improvement comprises the steps of:

(a) mixing a primary amine with said nitrogen-containing organic compound to provide a solution, (b) contacting the solution of step (a) with carbon monoxide, in the presence of a catalyst essentially free of redox active metal halide components and comprising rhodium or ruthenium at conditions sufficient to convert said nitrogen-containing organic compound into said carbamic acid derivative.

Said carbamic acid derivative may be a urethane or a urea (depending on whether a hydroxyl containing organic compound is included in the solution of step (a).) If the solution of step (a) includes only the nitrogen-containing compound and the primary amine—and any inert solvent—the carbamic acid derivative will be a urea, which may be separated and alcoholyzed to the urethane in a separate step.

Finally, the present invention provides a process for preparing a urethane by reacting a nitrogen-containing organic compound, selected from the group consisting of nitro, nitroso, azo and azoxy compounds, with carbon monoxide and a hydroxyl-containing organic compound, the improvement which comprises the steps of:

(a) adding a primary amine to a solution comprising said nitrogen-containing organic compound, (b) reacting said solution with carbon monoxide, in the presence of a catalyst consisting essentially of rhodium or ruthenium, (c) recovering a urethane, and (d) recovering a primary amine, in an amount equal or greater than the primary amine in the primary amine-containing solution of step (a).

Whether the process of the present invention is practiced to obtain urethane, directly, or upon separate alcoholysis of a urea, the primary amine recovered is equal to or greater than the primary amine initially provided in the reactant solution. Thus, in a continuous process, the primary amine can be constantly recycled and no further addition of primary amine, urea, hydrogen, etc. is needed to maintain the desired rate and selectivities.

While not wishing to be bound by theory, it appears that, in the rhodium or ruthenium-catalyzed carbonylation of the above nitrogen-containing organic compound to the corresponding urethane, in the absence of a redox-active metal halide co-catalyst, the urethane is produced by oxidative carbonylation of the corresponding primary amine. This oxidative carbonylation also provides hydrogen atom equivalents for the reduction of the nitrogen-containing organic compound to the primary amine. These reactions which are illustrated below (wherein [H] represents the rhodium or ruthenium hydrogen carrier) must be effectively coupled to provide the desired selectivity to the urethane.

Oxidative carbonylation: 

Reduction/hydrogenation: 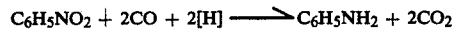

Net Reaction: 

Thus, the primary amine (illustrated by aniline) is an intermediate in the formation of urethane from the nitrogen-containing organic compound, but is not in net produced or consumed by the desired net reaction. It has been found that the primary amine is not in net consumed and the desired reaction stoichiometry is obtained even when primary amine is initially added to the reaction. It has been further found that the rate of conversion of nitrogen-containing organic compound to urethane and the selectivity of the reaction are increased when the initial amount of primary amine added to the reaction is increased. The initial amount of primary amine and its favorable effects on the rate and selectivity of the reaction persist for the conversion of an indefinite amount of nitrogen-containing organic compound to urethane.

The primary amine can be provided directly or by the in situ alcoholysis of a urea, biuret, or allophanate compound. Urea is alcoholyzed to form amine and urethane:

Biurets and allophanates similarly provide primary amine by alcoholysis under the reaction conditions.

In a carbonylation reaction wherein no primary amine, urea, biuret, or allophanate is present, initially, a fraction of the nitrogen-containing compound (e.g. nitrobenzene) can be reduced to the primary amine (aniline) by added hydrogen. It has been found that the reduction of the nitrogen-containing organic compound to a primary amine in the presence of hydrogen is rapid and provided that the molar ratio of hydrogen to the nitrogen-containing organic compound is less than 1, the remainder of the nitrogen-containing organic compound is converted to urethane by the desired reaction stoichiometry. The primary amine may also be provided in situ by the addition of water, in which case a fraction of the nitrogen-containing compound is reduced to primary amine by hydrogen equivalents obtained from shifting water and carbon monoxide to carbon dioxide.

In the initial absence of primary amine, hydrogen or water in a urethane production reaction, the hydrogen equivalents required to initially reduce nitrogen-containing organic compound to the primary amine are derived by dehydrogenation of the alcohol. (In the scheme illustrated below R represents a hydrogen or hydrocarbyl radical.)

Alcohol Dehydrogenation:  $R_2CHOH \longrightarrow R_2C=O + 2[H]$

Reduction/Hydrogenation:  $C_6H_5NO_2 + 2CO + 2[H] \longrightarrow C_6H_5NH_2 + 2CO_2$

---

Net Reaction  $C_6H_5NO_2 + 2CO + R_2CHOH \longrightarrow C_6H_5NH_2 + 2CO_2 + R_2C=O$ However, the carbonyl compounds which result from dehydrogenation of alcohol react with the primary amine to form undesired condensation products and water. Additional nitrogen-containing compound may then be reduced to the primary amine by hydrogen equivalents derived from water by the shift reaction.

When sufficient primary amine is initially present in the reaction solution, alcohol dehydrogenation is undesired because it converts the nitrogen-containing organic compound to primary amine and higher products instead of urethane. It has been found that methanol is less susceptible to dehydrogenation to the aldehyde than ethanol and higher alcohols, in the presence of the ruthenium catalysts utilized in the process of the instant invention. Therefore, the use of methanol improves the yield of urethane obtained in the carbonylation reaction product mixture and the combination of methanol and a primary amine in the process of the instant invention results in both an increased yield of urethane and an increased reaction rate.

Since oxidative carbonylation of amine to yield urethane and dehydrogenation of alcohol to carbonyl compound compete as sources of hydrogen equivalents for reduction of the nitrogen-containing organic compound, the selectivity of urethane production is increased by increasing the amine-to-alcohol ratio. The amine-to-alcohol ratio is increased by increasing the amine concentration and/or by decreasing the alcohol concentration. The primary amine may become the major reaction solution component and act as solvent. The alcohol concentration may be independently decreased by using an inert solvent in place of excess alcohol in the initial reaction solution.

It has been found that during the course of reactions in which amine is initially present, N,N'-disubstituted urea is present in the reaction mixture during the reaction. When nitrobenzene is reacted with alcohol, aniline, or many inert solvents as solvent, the N,N'-diphenyl-urea appears as a solid in samples of the reaction mixture which are cooled. The solid has been filtered from the solution components of such samples (including the soluble catalyst), and characterized as N,N'-diphenyl urea.

The amount of urea present during the reaction depends on the amine-to-alcohol ratio initially present. The higher the ratio, the higher the amount of urea present. When enough alcohol is provided, however, little or no urea persists to the end of the reaction. At the end of the reaction it is substantially reacted with alcohol to make urethane according to equation (4).

Some or perhaps all of the urethane appears to be formed via oxidative cabonylation to amine to urea, followed by urea alcoholysis:

$2C_6H_5NH_2 + CO \longrightarrow C_6H_5NHCONHC_6H_5 + 2[H]$ $C_6H_5NO_2 + 2CO + 2[H] \longrightarrow C_6H_5NH_2 + 2CO_2$

---

$C_6H_5NO_2 + C_6H_5NH_2 + 3CO \longrightarrow C_6H_5NHCONHC_6H_5 + 2CO_2$ then, $C_6H_5NHCONHC_6H_5 + ROH \longrightarrow C_6H_5NHCO_2R + C_6H_5NH_2$

---

$C_6H_5NO_2 + 3CO + ROH \longrightarrow C_6H_5NHCO_2R + 2CO_2$

If the amine-to-alcohol ratio becomes quite high or if insufficient alcohol is provided, urea will persist at the end of the reaction. If little or no alcohol is provided, urea will become the major reaction product. It can be seen that the urea production consumes one equivalent of initially added amine for each equivalent of urea produced. This consumed amine can be separately recovered by reacting the urea with the alcohol to make urethane in a separate step.

In a carbonylation reaction to produce urea, wherein no primary amine, urea, biuret or allophanate is present, initially, a fraction of the nitrogen-containing organic compound (e.g. nitrobenzene) can be reduced to the primary amine (aniline) by added hydrogen. Again, if the molar ratio of hydrogen to the nitrogen-containing organic compound is less than 1, the remainder of the nitrogen-containing organic compound is converted to urea by the desired reaction stoichiometry. In a batch process, an improved yield of urea is obtained when from 50 to about 60 percent of the nitrogen-containing organic compound is converted to primary amine, by hydrogenation, with the maximum being obtained at 50 percent conversion.

Since there is no alcohol present in the urea production reaction, side reactions of the alcohol (dehydrogenation, dehydration) which reduce selectivity are avoided. Thus, at the same initial amine concentration, the yield of urea in the absence of alcohol can exceed the yield of urethane in the presence of alcohol.

Because one equivalent of amine is consumed in the urea production reaction, the amine concentration decreases during the reaction, and the observed rate of nitrogen-containing organic compound conversion corespondingly decreases during the reaction. (If the molar ratio of nitrogen-containing organic compound to the primary amine is greater than 1, not all of the nitrogen-containing compound will be converted to urea. Thus, in the absence of alcohol, there will be unreacted nitrogen-containing organic compound left when all of the primary amine is consumed into urea. If the amine is used in large excess to the nitro compound (as solvent, for example) however, the fractional changes in amine concentration and rate of urea production are small or insignificant.

By providing amine at higher concentrations in excess of nitrogen-containing organic compound, the rate of urea production is increased and the nitro compound can be conveniently 100% converted. Urea yields near 100% may thus be obtained.

Since the urea alcoholysis to urethane is essentially quantitative, the overall selectivity of urethane synthesis can be increased by separating the urea synthesis and urea alcoholysis into two process steps, so that the selectivity reducing reactions of the alcohol in the catalytic carbonylation step are avoided.

DETAILED DESCRIPTION OF THE INVENTION

The nitrogen-containing organic compound useful in the process of this invention will contain at least one non-cyclic group in which a nitrogen atom is directly attached to a single carbon atom and through a double bond to oxygen or another nitrogen atom. The nitrogen-containing organic compound is selected from the group consisting of nitro, nitroso, azo and azoxy compounds.

Examples of suitable nitrogen-containing organic compounds for use in the process of this invention are compounds represented by the general formulae:

$$R(NO_x)_y \text{ and} \qquad \qquad I$$

$$R_1-RN=N(O)_z-R_2 \qquad \qquad II$$

wherein $R_1$ and $R_2$ are radicals independently selected from the group consisting of $C_1$ to $C_{20}$ hydrocarbyl radicals and substituted derivatives thereof, x is an integer of from 1 to 2, y is an integer of from 1 to 3, and z is an integer of from 0 to 1. The substituted hydrocarbyl radical may include hetero atoms selected from the group consisting of halogen, oxygen, sulfur, nitrogen and phosphorus atoms.

The nitrogen-containing compounds represented by formula I include nitro compounds (wherein x is 2) and nitroso compounds (wherein x is 1). Suitable nitro compounds are mononitro compounds such as nitrobenzene, alkyl and alkoxy nitrobenzenes wherein the alkyl group contains up to 10 carbon atoms, aryl and aryloxy nitrobenzenes, wherein the aryl group is phenyl, toyl, naphthyl, xylyl, chlorophenyl, chloronitrobenzenes, aminonitrobenzenes, carboalkoxyamino nitrobenzenes wherein the alkoxy group has up to 10 carbon atoms, aryl and aryloxy dinitrobenzenes, trinitro compounds such as trinitrobenzene, alkyl and alkoxytrinitrobenzenes, aryl and aryloxytrinitrobenzenes, the substituents being any of those already mentioned and chlorotrinitrobenzenes as well as similarly substituted mono and polynitro derivatives of the naphthalene, diphenyl, diphenylmethane, anthracene and phenanthrene series. Substituted or unsubstituted aliphatic nitro compounds such as nitromethane, nitrobutane, 2,2'-dimethyl nitrobutane, nitrocyclopentane, 3-methylnitrobutane, nitrooctadecane, 3-nitropropene-1, phenyl nitromethane, p-bromophenyl nitromethane, p-methoxy phenyl nitromethane, dinitroethane, dinitrohexane, dinitrocyclohexane, di-(nitrocyclohexyl)-methane are also suitable. The above nitro compounds may include more than one of the above substituents (in addition to the nitro group(s) such as in nitroaminoalkylbenzenes, nitroalkylcarboalkoxyamino benzenes, etc. From this group of nitro compounds nitrobenzene, nitrotoluene, dinitrobenzene, dinitrotoluene, trinitrobenzene, trinitrotoluene, mononitronaphthalene, dinitronaphthalene, 4,4'-dinitrodiphenylmethane, nitrobutane, nitrocyclohexane, p-nitrophenylnitromethane, dinitrocyclohexane, dinitromethylcyclohexane, dinitrocyclohexylmethane, nitroaminotoluene and nitrocarboalkoxyaminotoluene are preferred and in particular aromatic nitro compounds especially 2,4-and 2,6-dinitrotoluenes, meta and para dinitrobenzenes, and 5-nitro-2-methyl-carboalkoxyamino-, 2-nitro-5-methylcarboalkoxyamino-, and 3-nitro-2-methyl-carboalkoxyamino benzenes.

Examples of suitable nitroso compounds are the aromatic nitroso compounds such as nitrosobenzene, nitrosotoluene, dinitrosobenzene, dinitrosotoluene and the aliphatic nitroso compounds such as nitrosobutane, nitrosocyclohexane and dinitrosomethylcyclohexane.

The nitrogen-containing compounds represented by Formula II include both azo compounds (wherein z is 0) and azoxy compounds (wherein z is 1). Suitable compounds represented by Formula II include azobenzene, nitroazobenzne, chloroazobenzene, alkyl or aryl substituted azobenzene, azoxybenzene, nitroazoxybenzene, chloroazoxybenzene, etc.

The primary amine compound utilized in this invention may be selected from the group consisting of compounds represented by the general formula:

$$R_1(NH_2)_Y \qquad \qquad IV$$

wherein $R_1$ and Y are as defined above. Examples of such primary amines include methylamine, ethylamine, butylamine, hexylamine, ethylenediamine, propylenediamine, butylenediamine, cyclohexylamine, cyclohexyldiamine, aniline, p-toluidine, o-m-and p-diaminobenzenes, aminomethylcarbanilic acid esters, especially the 5-amino-2 methyl-, 2-amino-5-methyl-, and 3-amino-2-methyl carboalkoxyaminobenzenes, wherein said alkoxy group has up to 10 cabon atoms, o-, m- and p-nitroanilines, nitroaminotoluenes, especially those designated above, o-and p-phenylenediamine, benzylamine, o-amino-p-xylene, 1-aminophthaline, 2,4-and 2,6-diaminotoluenes, 4,4'-diaminodibenzyl, bis (4-aminophenyl) thioether, bis (4-aminophenyl) sulfone, 2,4,6-triaminotoluene, o-, m-and p-chloroanilines, p-bromoaniline, 1-fluoro-2,4diaminobenzene, 2,4-diaminophenetole, o,-m- and-paminoanisoles, ethyl p-aminobenzoate, 3-aminophthalic anhydride, etc. These primary amino compounds may be used alone or in combination.

Among the above-enumerated primary amino compounds, those which can be derived from the starting nitro compound are preferred. For example, when nitrobenzene is used as the starting aromatic nitro compound, aniline is preferred. Similarly, 2-amino-4-nitrotoluene, 4-amino-2-nitrotoluene, and 2,4-diaminotoluene are preferably used when the starting aromatic nitro compound is 2,4-dinitrotoluene, while 2-amino-6-nitrotoluene, and 2,6-diaminotoluene are preferably used when the starting aromatic nitro compound is 2,6-dinitrotoluene.

The primary amine compound can be provided by the insitu decomposition of the corresponding urea or biuret as represented by compounds having the general formulae:

$$RNH-\underset{\underset{O}{\|}}{C}-NHR_1$$

and

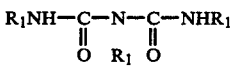

respectively, wherein $R_1$ is as defined above. Of course, since the above urea and biuret will comprise more than one radical, $R_1$ may represent different radicals in the same compound. That is non-symmetrical ureas and biurets, e.g.

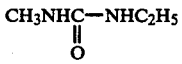

are within the scope of the invention.

In the process of this invention, no particular limitation is placed on the amount of primary amine used. However, it is preferably used in an amount equal to from 0.1 to 100 moles per gm-atom of nitrogen in the nitrogen-containing organic compound.

The process of the invention may be carried out in the absence of solvent but the use of a solvent is not precluded. Suitable solvents include, for example, aromatic solvents such as benzene, toluene, xylene, etc.; nitriles such as acetonitrile, benzonitrile, etc.; sulfones such as sulfolane, etc.; halogenated aliphatic hydrocabons such as 1,1,2-trichloro-1,,2,2.-trifluoroethane, etc.; halogenated aromatic hydrocarbons such as monochlorobenzene, dichlorobenzene, trichlorobenzene, etc.; ketones; esters; and other solvents such as tetrahydrofuran, 1,4-dioxane, 1,2-dimethoxyethane, etc.

The hydroxy-containing organic compounds for use in the process of this invention include compounds represented by the general formula

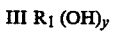 III $R_1(OH)_y$ III wherein $R_1$ and y are defined above.

Hydroxy compounds suitable for use in the process of the present invention may be, for example, mono- or polyhydric alcohols containing primary, secondary or tertiary hydroxyl groups as well as mono- and polyhydric phenols. Mixtures of these hydroxy compounds may also be used. The alcohols may be aliphatic or aromatic and may bear other substituents in addition to hydroxyl groups but the substituents should (except as hereinafter described) preferably be non-reactive to carbon monoxide under the reaction conditions. Especially suitable compounds are phenol and monohydric alcohols such as methyl, ethyl, n- and sec-propyl, n-, iso, sec-and tert butyl, amyl, hexyl, lauryl, cetyl, benzyl, chlorobenzyl and methoxybenzyl alcohols as well as diols such as ethylene glycol, diethylene glycol, propylene glycol and dipropylene glycol, triols such as glycerol, trimethylol propane, hexanetriol, tetrols such as pentaerythritol and the ethers of such polyols providing that at least one hydroxyl group remains unetherified. The etherifying group in such ether alcohols normally contains up to 10 carbon atoms and is preferably an alkyl, cycloalkyl or aralkyl group which may be substituted with, for example, a halogen or an alkyl group.

The most preferred hydroxyl-containing organic compound for use in the process of this invention is methyl alcohol or a similar lower alkanol, e.g. a $C_1$ to $C_5$ alcohol.

The process of this invention includes the use of any mixture of nitro compounds, nitroso compounds, azo or azoxy compounds with any mixture of hydroxy compounds and also the use of compounds containing both functions, i.e. hydroxynitro compounds, hydroxynitroso compounds, hydroxyazo and hydroxyazoxy compounds such as 2-hydroxynitroethane, 2-hydroxynitrosoethane, nitrophenols, nitronaphthols, nitrosophenols, nitrosonaphthols, hydroxyazobenznes and hydroxyazoxybenzenes. Mixtures of these nitrogen-containing compounds may also be used.

This process of the invention has been found to proceed most smoothly to give the highest yields when employing nitro compounds. It is accordingly preferred to use nitro compounds rather than nitroso, azo or azoxy compounds.

The catalyst utilized in the process of this invention may be selected from the group consisting of rhodium or ruthenium salts, e.g. the halides, nitrate, sulfate, acetate, formate, carbonate, etc. and rhodium or ruthenium complexes (especially rhodium or ruthenium carbonyl complexes) including ligands capable of coordinating with the rhodium or ruthenium atom. The complex may include one or more rhodium or ruthenium atoms and suitable ligands may include carbon-carbon unsaturated groups as in ethylene, isobutylene, cyclohexene, norbornadiene, cyclooctatetraene. Other suitable ligands include acetylacetonate (acac), hydrogen atoms, carbon monoxide, nitric oxide, alkyl-radicals, alkyl or aryl nitriles or isonitriles, nitrogen-containing heterocyclic compounds such as pyridine, piperidine, and organo phosphines, arsines or stilbines.

In one embodiment of this invention a rhodium or ruthenium catalyst for use in the present process further comprises a polyamino ligand having at least two tertiary amino groups capable of coordinating with rhodium. For example, such polyamino ligand may be selected from the group of compounds represented by the general formula:

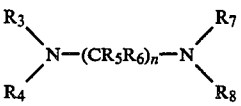

wherein $R_3$, $R_4$, $R_7$ and $R_8$, which may be the same or different, each represent an alkyl, aryl, alkaryl or aralkyl group which may be substituted by one or more inert substituents or $R_3$ and $R_4$ and/or $R_7$ and $R_8$ may form a ring structure together with the atom N to which they are attached; $R_5$ and $R_6$, which may be the same or different, each represent a hydrogen atom or a lower alkyl group and may form a ring structure together with the atom N and $R_3$, $R_4$, $R_7$ and/or $R_8$ and n is an integer, preferably n varies from 1 to about 5, e.g. 1 to 3.

Examples of ligands according to the general formula are 1,2-bis(diethylamino)ethane 1,2-bis(dimethylamino)propane, 1,2-bis(dimethylamino)ethane, 1,2-bis(di-t-butylamino)ethane, 1,2-bis(diphenylamino)ethane, 1,2-bis(diphenylamino)propane, 1,2-bis(diphenylamino)butane, 2,2′-bipyridine, 2,2′-biquinoline, bispyridylglyoxal, and 1,10-phenanthroline and derivatives thereof. Preference is given to the use of 2,2′-bipyridine and 1,10-phenanthroline.

In another embodiment of the instant invention the catalyst utilized in the process of this invention may comprise a bis-phosphino rhodium or ruthenium compound. The bis-phosphino rhodium or ruthenium compound may also include the above anions, i.e. sulfate, acetate, trifluoroacetate, formate, carbonate, etc. and-/or other ligands, discussed above, cpable of coordinating with the rhodium or ruthenium atom. The bis-phosphino rhodium or ruthenium compound may include more than one rhodium or ruthenium atom.

The bis-phosphino ligand of the rhodium or ruthenium catalyst may be represented by the general formula:

$$(R_3)(R_4)P-R_9-P(R_7)(R_8)$$

wherein $R_3$, $R_4$, $R_7$ and $R_8$ are as defined above and $R_9$ is a divalent radical providing sufficient spacing to enable both phosphorus atoms to coordinate with a rhodium or ruthenium atom. $R_9$ may be a hydrocarbyl having from 1 to 10 atoms or a substituted derivative thereof including one or more heteroatoms selected from the group connsisting of halogen, oxygen, sulfur, nitrogen, and phosphorus atom. Preferably, $R_9$ comprises from 2 to 6 carbon atoms.

Examples of suitable bis phosphine ligands include bis(1,2-diphenylphosphino)benzene, bis(1,2-diphenylphosphino)-ethane, bis(3,3diphenylphosphino)propane, etc.

Examples of ruthenium compounds which are suitable as catalysts for the process of this invention include:
Ru(CO)$_3$[bis(1,2-diphenylphosophino)ethane]
Ru(CO)$_3$[bis(1,2-diphenylphosphino)benzene]
Ru(CO)$_3$[bis(1,3-diphenylphosphino)propane]

The rhodium or the ruthenium catalyst is preferably utilized as a homogeneous catalyst and therefore one criteria for the selection of the rhodium or ruthenium compound is its solubility under the conditions of reaction in the mixture of the nitrogen-containing organic compound and the primary amino compound (and, if desired, the hydroxyl-containing organic compound). The rhodium or ruthenium compound is also selected with a view toward the catalytic activity of the compound. Mixtures of rhodium and ruthenium compounds may be used.

The rhodium or ruthenium compound comprising a polyamino ligand or a bis-phosphino ligand may be preformed or formed in situ in the reaction solution by separately dissolving a rhodium or a ruthenium compound and the respective ligand. Since the catalyst is utilized in very low concentration, it is preferred that the compound is preformed to ensure that such ligand will be coordinated with the rhodium or ruthenium during the reaction.

The rhodium or ruthenium catalyst may be used in mixture with co-catalysts or promoters so long as the co-catalyst, unlike the redox-active metal halide co-catalysts of the prior art, does not change the reactivity of the catalyst system to consume added amines. Mono-tertiary amines are one class of suitable promoters for the rhodium catalysts of this invention. Suitable mono-tertiary amines are those described in U.S. Pat. No. 3,993,685 herein incorporated by reference. Preferably the catalyst is free of halide to avoid corrosion problems.

In carrying out the process of the invention, the hydroxyl-containing organic compound and carbon monoxide may be used in amounts equal to at least 1 mole per gm-atom of nitrogen in the nitrogen-containing compound. When it is desired to obtain the urethane product, directly, preferably the hydroxyl-containing organic compound is used in excess. When it is desired to obtain a urea product, then the primary amine is, preferably, used in excess.

The amount of the rhodium or ruthenium compound used as the catalyst may vary widely according to the type thereof and other reaction conditions. However, on a weight basis, the amount of catalyst is generally in the range of from $1 \times 10^{-5}$ to 1 part, and preferably from $1 \times 10^{-4}$ to $5 \times 10^{-1}$ parts, per gram-atom of nitrogen in the starting nitrogen-containing organic compound when expressed in terms of its metallic component.

The reaction temperature is generally held in the range of 80° to 230° C., and preferably in the range of from 100° to 200° C.

The reaction pressure, or the initial carbon monoxide pressure, is generally in the range of from 10 to 1,000 kg/cm$^2$G, and preferably from 30 to 500 kg/cm$^2$G.

The reaction time depends on the nature and amount of the nitrogen-containing organic compound used, the reaction temperature, the reaction pressure, the type and amount of catalyst used, the type of reactor employed, and the like, but is generally in the range of from 5 minutes to 6 hours. After completion of the reaction, the reaction mixture is cooled and the gas is discharged from the reactor. Then, the reaction mixture is subjected to any conventional procedure including filtration, distillation, or other suitable separation steps, whereby the resulting urethane or urea is separated from any unreacted materials, any by-products, the solvent, the catalyst, and the like.

The urethanes and the ureas prepared by the process of the invention have wide applications in the manufacture of agricultural chemicals, isocyanates, and polyurethanes.

The invention is more fully illustrated by the following examples. However, they are not to be construed to limit the scope of the invention.

In each of the following examples, the reaction was conducted in batch mode in a 300 ml stainless steel autoclave reactor equipped with a stirring mechanism which provides constant dispersion of the gas through the liquid solution. Heating of the reaction is provided by a jacket-type furnace controlled by a proportioning controller. The autoclave is equipped with a high pressure sampling system for removal of small samples of the reaction solution during the reaction in order to monitor the reaction progress. Reaction solutions were prepared and maintained under anaerobic conditions. Reaction samples were analyzed by gas chromatography.

The following examples are shown for the purpose of illustration only and should not be deemed as limiting the scope of the invention.

EXAMPLE 1

75 ml of a solution containing 12.31 g (0.100 mole) nitrobenzene, 4.66 g (0.050 mole) aniline, and 2.68 g t-butylbenzene (internal standard for gas chromatographic analysis) in methanol and 0.128 g (0.20 millimole) Ru$_3$(CO)$_{12}$ were placed in the reaction vessel. The gas volume in the vessel was replaced with carbon monoxide at 1000 psig at ambient temperature. The reactor contents were then heated to 160° C. Complete conversion of nitrobenzene occurred over 8.5 hours at 160° C. and yielded 0.076 mole methyl N-phenyl carbamate (76% selectivity based on nitrobenzene) and 0.067 mole aniline (17% selectivity to additional aniline based on nitrobenzene). The balance consisted of undesired side-products formed by aniline-formaldehyde condensations and ensuing reactions.

EXAMPLE 2

The procedure was the same as for Example 1 except that 9.32 g (0.100 mole) aniline was initially provided to the reaction. The volume of methanol ws reduced so that the total solution volume was again 75 ml. Complete conversion of nitrobenzene occurred over 3.5 hours at 160° C. and yielded 0.088 mole methyl N-phenylcarbamate (88% selectivity based on nitrobenzene) and 0.112 mole aniline (12% selectivity to additional aniline based on nitrobenzene).

COMPARATIVE EXAMPLE 1

The procedure was the same as for Example 1 with the exception that no aniline was introduced to the reaction. Complete nitrobenzene conversion required 26 hours at 160° C. Selectivities based on nitrobenzene were 38 percent to methyl N-phenylcarbamate, 32 percent to aniline, 12 percent total to formylidene aniline and N-methylaniline. The balance was converted to higher molecular weight products derived from aniline.

It can be seen by comparison of Examples 1, 2 and Comparative Example 1 that the rate and selectivity of the reaction are improved by initially providing increasing amounts of amine to the reaction.

Relative to Example 1 and 2, the amine concentration and amine-to-alcohol ratio may be further increased by replacing more alcohol in the initial solution with amine. Amine may become the major reaction solution component and thus act as solvent for the reaction.

The amine-to-alcohol ratio may also be increased by simply replacing some of the excess alcohol with an inert solvent.

EXAMPLE 3

The procedure was the same as Example 1 except only 6.40 g (0.200 mole) methanol was initially provided to the reaction solution. Toluene was added as an inert solvent to again give a total solution volume of 75 ml. Complete conversion of nitrobenzene occurred in 8.5 hours at 160° C. yielding 0.095 mole methyl N-phenyl carbamate (95% selectivity based in nitrobenzene) and 0.054 mole aniline (4% selectivity to additional aniline based on nitrobenzene).

It can be seen by comparison of Examples 1 and 3 that reducing the alcohol concentration in the solution, for example by using an inert solvent, increases the selectivity of the reaction without any decrease in the rate of urethane production. Thus, in Example 1, wherein the ratio of methanol to nitrobenzene was 15:1, the selectivity was 76%, while in this Example, wherein the ratio of methanol to nitrobenzene was 2:1, the selectivity was increased to 95%. (Decreasing the ratio of methanol to nitrobenzene to almost 1:1, would be expected to further increase selectivity.) In view of the above, it is preferable to provide a ratio of methanol (or other hydroxy-containing organic compound) to nitrobenzene (or other nitrogen-containing organic compound) of less than 15:1, more preferably a ratio of from 1:1 to 5:1, most preferably a ratio of from 1:1 to 3:1, e.g. about 2:1.

EXAMPLE 4

The procedure was the same as for Example 3 except that no methanol is provided to the reaction. Additional toluene solvent was added to again give 75 ml total reaction solution. After 10 hours at 160° C., 0.048 mole nitrobenzene and 0.008 mole aniline remained (52% and 42% conversion, respectively). The mixture contained copious amounts of a white organic colid. After cooling, the solid was filtered and characterized (IR, NMR) as predominantly N,N'-diphenyl urea. The spectra and the excess consumption of nitrobenzene over aniline indicate that N,N',N"-triphenylbiuret was also present.

During the course of the urea synthesis of Example 4, the observed rates of nitrobenzene and aniline conversion decreased as the aniline was consumed. However, the aniline-dependent rate of nitrobenzene conversion to urea in this experiment was approximately equal to the aniline-dependent rates of nitrobenzene conversion to urethane in the experiments of Examples 1 and 4. This shows that urea synthesis is kinetically competent to account for all of urethane synthesis in the presence of alcohol.

EXAMPLE 5

10.60 g (0.050 mole) N,N'-diphenylurea and methanol to give 75 ml total mixture volume were heated from room temperature to 160° C. over approximately one hour. On reaching 160° C., the mixture contained 0.035 mole each of methyl N-phenyl carbamate and aniline, and unreacted N,N'-diphenylurea. After 45 minutes at 160° C., the solution contained 0.050 mole each of methyl N-phenyl carbamate and aniline, representing quantitative urea alcoholysis.

From this example, it can be seen that the urea alcoholysis occurs in the absence of an added catalyst. The data obtained also indicate that uncatalyzed urea alcoholysis is kinetically competent to account for all of the urethane synthesis in the catalytic conversion of nitro compounds in the presence of alcohol.

EXAMPLE 6

The procedure was the same as for Example 1 except that 0.23 g (1.40 millimole) tetraethylammoniumchloride was also provided to the reaction. Complete conversion of nitrobenzene occurred over 6.0 hours at 160° C. and yielded 0.077 mole methyl N-phenylcarbamate (77% selectivity based on nitrobenzene) and 0.071 mole aniline (21% selectivity to additional aniline based on nitrobenzene).

COMPARATIVE EXAMPLE 2

The procedure was the same as for Example 6 except that no aniline was initially provided to the reaction. Commplete nitrobenzene conversion required 15 hours at 160° C. Selectivities based on nitrobenzene were 60% to methyl N-phenylcarbamate and 34% to aniline.

Comparison of Example 6 with Comparative Example 2 shows that the rate and selectivity of the reaction are improved by initially providing primary amine to the reaction, when the reaction also includes chloride ion. Example 6 also shows that the amine is not, in net, consumed when the reaction contains chloride ion. Thus, in the prior art processes in which the amine is consumed in the presence of redox-active metal chloride co-catalysts, it is the additional presence of the redox-active metal which causes the amine consumption.

EXAMPLE 7

75 ml of a solution containing 3.07 g (0.025 mole) nitrobenzene, 11.64g (0.125 mole) aniline, and 2.74 g t-butylbenzene (internal standard) in toluene and 0.128 g (0.20 millimole) Ru$_3$(CO)$_{12}$ were placed in the reaction vessel. The gas in the vessel was replaced with carbon monoxide at 1000 psig at ambient temperature. The reactor contents were then heated to 160° C. After 1.5 hours at 160° C., the reactor contents were cooled to ambient temperature. The sampling system was clogged with solid N,N'-diphenylurea. 30 ml of methanol was then injected into the vessel and the gas in the vessel was vented and replaced with nitrogen at 1000 psig. The reactor contents were then reheated to 160° C. After 1.0 hour at 160° C., the reactor contents were cooled. The resulting solution contained no nitrobenzene, 0.023 mole methyl N-phenylcarbamate (92% selectivity on nitrobenzene) and 0.126 mol aniline.

COMPARATIVE EXAMPLE 3

The procedure was the same as for Example 7 except that no aniline was initially provided to the reaction. Additional toluene solvent was added to again give a total initial solution volume of 75 ml. After 1.5 hours at 160° C. under carbon monoxide, 0.023 mole nitrobenzene remained and no products were observed by the gas chromatographic analytical system. The mixture was cooled, methanol was added, and the gas was changed to nitrogen as in Example 7. After 1.0 hours at 160° C. under nitrogen, the solution contained 0.013 mole nitrobenzene, 0.003 mole aniline, 0.001 mole N-methylene aniline, 0.004 mole N-methyl aniline, and less than 0.001 mole methyl N-phenyl carbamate.

What is claimed is:

1. A process for reacting a solution containing a nitrogen-containing organic compound, selected from the group consisting of nitro, nitroso, azo and azoxy compounds, with carbon monoxide to obtain a carbamic acid derivative selected from the group consisting of urethane and N,N'-disubstituted urea, which comprises providing a primary amine in said solution and reacting said nitrogen-containing organic compound with carbon monoxide in the presence of a catalyst selected from the group consisting of ruthenium and rhodium, and essentially free of redox-active metal components; with the proviso that, in a batch process, when said carbamic acid derivative is an N,N'-disubstituted urea and said primary amine is provided by the in-situ reduction of the nitrogen-containing organic compound, by hydrogen, to said primary amine, then from 50 to about 60 percent of said nitrogen-containing organic compound is hydrogenated to maximize the yield of said N,N'-disubstituted urea.

2. The process of claim 1 wherein said nitrogen-containing organic compound is a nitro compound.

3. The process of claim 2 wherein said nitro compound is an aromatic nitro compound.

4. The process of claim 3 wherein said primary amine is an aromatic amine corresponding to said aromatic nitro compound.

5. The process of claim 4 wherein said catalyst is selected from the group consisting of rhodium and ruthenium carbonyl complexes.

6. The process of claim 4 wherein said N,N'-disubstituted urea is recovered and subsequently converted to a urethane by alcoholysis in the presence of a hydroxyl-containing organic compound.

7. The process of claim 3 wherein said nitrogen-containing organic compound is carbonylated in the presence of a hydroxyl-containing organic compound and said carbamic acid derivative is a urethane.

8. The process of claim 6 further comprising recovering a primary amine, upon alcoholysis of said urea, in an amount equal to or greater than the primary amine initially provided in the solution.

9. The process of claim 7 further comprising recovering a primary amine in an amount equal to or greater than the primary amine initially provided in the solution.

10. The process of claim 7 wherein said hydroxyl-containing organic compound is methanol.

11. The process of claim 5 wherein said catalyst comprises a bisphosphino ligand.

12. The process of claim 5 wherein said catalyst comprises a poly tertiary amino ligand.

13. The process of claim 7 wherein the molar ratio of said hydroxyl-containing organic compound to said aromatic nitro compound is less than 15:1.

14. The process of claim 7 wherein the molar ratio of said hydroxyl-containing organic compound to said aromatic nitro compound is between 1:1 and 3:1.

15. The process of claim 3 wherein said aromatic nitro-compound is selected from the group consisting of nitrobenzene, nitroanisole, dinitrotoluene, nitromesitylene, bis(4-nitro-phenyl) methane, nitroaminotoluene and nitrocarboalkoxyaminotoluene.

16. The process of claim 15 wherein said primary amine is selected from the group consisting of p-toluidine, aniline, diaminotoluene, bis(4-aminophenyl) methane, aminonitrotoluene, and aminomethylcarboalkoxybenzene.

17. The process of claim 2 wherein said nitro containing organic compound is converted into the corresponding carbamic acid derivative, by reacting said nitrogen-containing organic compound with carbon monoxide at a temperaure of from about 100° C. to 200° C. and a carbon monoxide pressure in the range of from 30 to 500 kg./cm$^2$G.

18. The process of claim 6 wherein the molar ratio of the primary amine and the nitrogen-containing organic compound is greater than 1:1.

19. The process of claim 13 wherein said solution further comprises an inert solvent.

* * * * *